US00PP20441P3

(12) United States Plant Patent
Stemkens

(10) Patent No.: US PP20,441 P3
(45) Date of Patent: Oct. 27, 2009

(54) *CUPHEA* PLANT NAMED 'CUPED'

(50) Latin Name: *Cuphea hybrida*
Varietal Denomination: Cuped

(75) Inventor: Henricus G. W. Stemkens, Andijk (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/002,824

(22) Filed: Dec. 19, 2007

(65) Prior Publication Data

US 2009/0165180 P1 Jun. 25, 2009

(51) Int. Cl.
*A01H 5/00* (2006.01)

(52) U.S. Cl. ..... Plt./420

(58) Field of Classification Search ..... Plt./420
See application file for complete search history.

(56) References Cited

OTHER PUBLICATIONS

PW Proven Winners Totally Tempted *Cuphea llavea* [online] [retrieved on Oct. 20, 2008]. Retrieved from the Internet <http://www.provenwinners.com/plants/detail.cfm?photoID=8728> 2pp.*

* cited by examiner

*Primary Examiner*—June Hwu
(74) *Attorney, Agent, or Firm*—S. Matthew Edwards

(57) ABSTRACT

A new *Cuphea* plant, particularly distinguished by its deep red flower color and compact plant habit.

1 Drawing Sheet

Latin name of the genus and species of the plant claimed: *Cuphea hybrida.*

Varietal denomination: 'Cuped'.

BACKGROUND OF THE NEW PLANT

The present invention comprises a new distinct cultivar of *Cuphea,* botanically known as *Cuphea hybrida.*

The new *Cuphea* is a product of a planned breeding program conducted in Enkhuizen, Netherlands. The new *Cuphea* cultivar is early flowering, has a compact plant habit, and a deep red flower color.

The new *Cuphea* is propagated by cuttings resulting from a single seedling. This seedling originates from a selection in *Cuphea* 'D0369-1' (not patented) pollinated with an unknown male parent. Seeds of this cross were sown in spring 2003 in Enkhuizen, Netherlands. The seedling was selected in August 2003 in Enkhuizen.

The present cultivar has been repeatedly asexually reproduced by cuttings in Enkhuizen, Netherlands, since 2003. The distinctive characteristics of this new *Cuphea* are stable and reproduced true to type in successive generations of asexual reproduction.

The new *Cuphea* plant is a perennial in zones 8 to 9 in the US.

DESCRIPTION OF THE DRAWING

The new *Cuphea* plant is illustrated by the accompanying photographic drawing which shows blooms, buds and foliage of the plant in full color, the color showing being as true as can be reasonably obtained by conventional photographic procedures.

BOTANICAL DESCRIPTION OF THE PLANT

The following detailed descriptions set forth the distinctive characteristics of this new *Cuphea.* The data which defines these characteristics were collected from asexual reproductions carried out in Enkhuizen, Netherlands. The plant history was taken from 13 week old plants. The instant plant was grown in an 11 cm container in an outdoor container field.

Color references are primarily to the R.H.S. Colour Chart of The Royal Horticultural Society of London.

Plants of the new *Cuphea* differ primarily from the plants of the originator 'D0369-1' in the following characteristics:

Flowers of the new variety are deep red colored whereas plants of the parent are rose colored. Plants of the new variety flower very early whereas plants of the parent flower late. Flowers of the new variety are bigger than the flowers of the parent.

TABLE 1

DIFFERENCES BETWEEN THE NEW CULTIVAR 'CUPED' AND A SIMILAR CULTIVAR

| | 'Cuped' | 'Flamenco Rumba' (U.S. Plant Pat. No. 17,213) |
|---|---|---|
| Plant height | 20 cm | 40 cm |
| Flower size | 26 mm | 22 mm |
| Plant width | 20 cm | 30 cm |

The Plant:

*Classification — botanical.*—Cuphea hybrida.

Parentage:

*Parent selection.*—'D0369-1' (Not patented).

Propagation:

*Type of cutting.*—Terminal cuttings.

*Time to initiate roots.*—6–12 days at 18° C.

*Time to produce a rooted cutting.*—10 days.

*Root description.*—Fine, fibrous and light yellow in color.

Plant description:

*Form.*—Globular, symmetrical, mounded.

*Height.*—20 cm.

*Plant diameter.*—24 cm.

*Branching habit.*—Freely basal branching.

The stem:

*Shape.*—Round.

*Color.*—137B.

*Texture.*—Pubescent.

*Length.*—15–20 cm.

*Diameter.*—4–6 mm.

*Internode length.*—20–30 mm.

*Quantity.*—Approximately 25 per plant.

The foliage:

*Type.*—Simple.

*Arrangement.*—Alternate.

*Number of leaves per stem.*—15–25.

*Size of leaf.*—Length: 18 mm. Width: 10 mm.

*Shape of leaf.*—Elliptic.

*Leaf venation.*—37B.

*Shape of apex.*—Acute.

*Shape of base.*—Obtuse.

*Texture — Upper and lower surfaces.*—Pubescent.

*Margin.*—Entire.

*Venation.*—Pinnate.

*Fragrance.*—Present, musky.

*Color.*—Upper surface: 137B. Lower surface: 137D.

*Petiole.*—Absent.

The flower:

*Natural flowering season.*—From April until October.

*Inflorescences.*—Spike.

*Number of flowers per spike.*—3–5.

*Form.*—Close to salverform.

*Appearance.*—Single flowers.

*Aspect.*—Facing upward or outward.

*Flower size.*—Diameter: 4 mm. Depth: 16 mm.

*Disc diameter* (*whole corolla).*—18 mm.

*Number of flowers per plant.*—360.

*Flower opening/closing behavior.*—Flowers stay open permanently.

*Fragrance.*—Present, sweet.

*Bud* (*just before flowering*).—Shape: Oval. Diameter: 2 mm. Length: 4 mm. Color: 138B. Texture: Pubescent.

*Pedicel.*—Color: 138B. Shape: Cylindrical. Length: 3–6 mm. Diameter: 1 mm. Texture: Pubescent.

*Corolla tube.*—Corolla tube color (outer surface): 83B. Petal color (outer surface): 45A. Corolla tube length: 22 mm. Corolla tube diameter: 4 mm. Tube shape: Tubular. Tube apex: Flared. Tube base shape: Spurred, the spur has a length of 1 mm and width of 1 mm. Surface texture of the outer corolla tube: Very pubescent. Petals: Apetalous. Calyx: Absent. Valvate lobe number: 6 sub-equal valvate lobes, 4 large and 2 small. Valvate lobes attachment: Individual valvate lobes are attached at summit of hypanthium. Large valvate lobe dimensions: 9 mm in width and 11 mm in length. Small valvate lobe dimensions: 2 mm in width and 4 mm in length. Valvate lobe color: 45B. Valvate lobe texture: Smooth. Valvate lobe appearance (adaxial and abaxial surfaces): Irridescent. Valvate lobe shape: Rotund, unfused. Valvate lobe apex: Obtuse. Valvate lobe base: Cuneate and rounded. Valvate lobe margin: Close to sinuous.

*Lasting quality of flowers.*—On the plant: 3 days. Cut flowers: 10 hours.

Reproductive organs:

*Androecium.*—Stamens quantity: 8. Anther shape: Ovoid. Anther length: 2 mm. Anther color: 144C. Pollen amount: No pollen.

*Gynoecium.*—Pistil quantity: 1. Pistil length :1 mm. Stigma shape: Bi-lobed. Stigma color: 144C. Style length: 14 mm. Style color: 144D. Ovary color: 144C.

Seed development: No seed set has been observed to date.

Disease resistance: No disease/pest resistance has been observed to date.

Weather tolerance: Heat tolerant to 42° C.; susceptible to wet conditions.

What is claimed is:

1. A new and distinct cultivar of *Cuphea* plant named 'Cuped', as substantially illustrated and described herein.

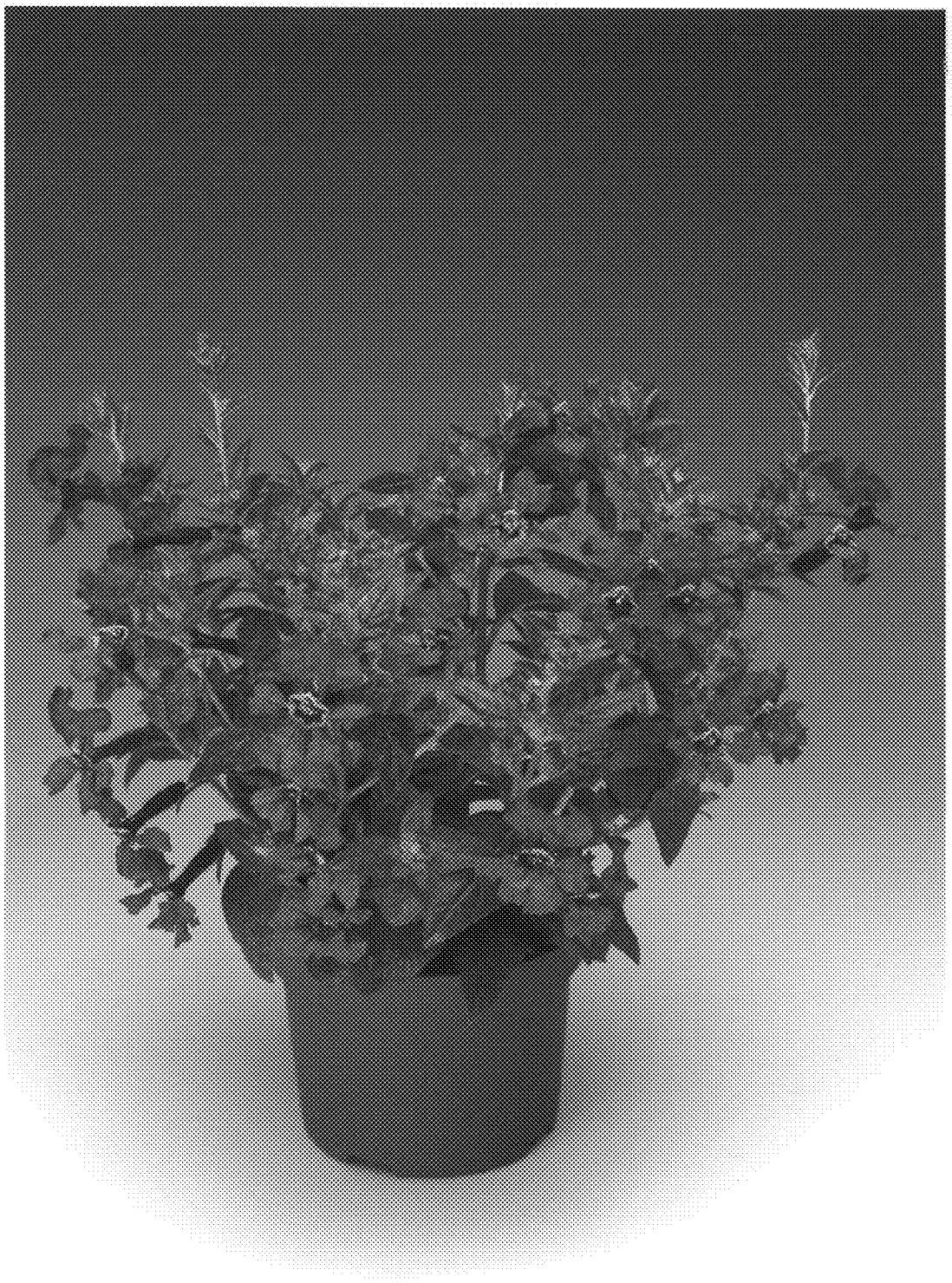

* * * * *